(12) United States Patent
Bercoff et al.

(10) Patent No.: US 12,245,889 B2
(45) Date of Patent: Mar. 11, 2025

(54) ULTRASOUND IMAGING SYSTEM

(71) Applicant: SUPERSONIC IMAGINE, Aix en Provence (FR)

(72) Inventors: Jessica Bercoff, Aix en Provence (FR); Matthieu Valentin, Marseilles (FR); Pascal Roncalez, Eguilles (FR)

(73) Assignee: SUPERSONIC IMAGINE, Aix en Provence (FR)

( * ) Notice: Subject to any disclaimer, the term of this patent is extended or adjusted under 35 U.S.C. 154(b) by 696 days.

(21) Appl. No.: 17/041,562

(22) PCT Filed: Apr. 24, 2018

(86) PCT No.: PCT/IB2018/000580
§ 371 (c)(1),
(2) Date: Sep. 25, 2020

(87) PCT Pub. No.: WO2019/207331
PCT Pub. Date: Oct. 31, 2019

(65) Prior Publication Data
US 2021/0022708 A1    Jan. 28, 2021

(51) Int. Cl.
*A61B 8/00* (2006.01)
*G06F 3/0354* (2013.01)
(Continued)

(52) U.S. Cl.
CPC ............ *A61B 8/467* (2013.01); *A61B 8/4405* (2013.01); *A61B 8/462* (2013.01); *A61B 8/463* (2013.01);
(Continued)

(58) Field of Classification Search
CPC ....... A61B 8/4405; A61B 8/462; A61B 8/463; A61B 8/465; A61B 8/467;
(Continued)

(56) References Cited

U.S. PATENT DOCUMENTS

| | | | |
|---|---|---|---|
| 5,250,929 A | 10/1993 | Hoffman et al. | |
| 6,135,958 A | 10/2000 | Mikula-Curtis et al. | |

(Continued)

FOREIGN PATENT DOCUMENTS

| | | |
|---|---|---|
| CN | 201266371 Y | 7/2009 |
| CN | 101675410 | 3/2010 |

(Continued)

OTHER PUBLICATIONS

Dumont, Douglas M. et al., "Feasability of a ARFI/B-mode/Doppler system for real-time, freehand scanning of the cardiovascular system", Medical Imaging 2011: Ultrasonic Imaging, Tomography, and Therapy, SPIE, 1000 20th Street, Bellingham WA 98225-6705, USA, vol. 7968, No. 1, Mar. 3, 2011, pp. 1-12.

(Continued)

*Primary Examiner* — Michael T Rozanski
(74) *Attorney, Agent, or Firm* — Merchant & Gould P.C.

(57) ABSTRACT

An ultrasound imaging system (10) comprising probe (20), a processing unit (30) for processing an image, a display (50) for visualizing the image, and a control panel (40) for configuring and controlling the processing unit. The control panel comprises input control elements (41) and a touch pad (42). The touch pad is a multi-touch device providing multi-touch information of at least two or more touch of user on the touch pad for determining a gesture and an associated system function.

19 Claims, 4 Drawing Sheets

(51) Int. Cl.
    *G06F 3/041* (2006.01)
    *G06F 3/0488* (2022.01)
    *G06F 3/04883* (2022.01)
    *G06F 3/04886* (2022.01)

(52) U.S. Cl.
    CPC ........ *G06F 3/03547* (2013.01); *G06F 3/0412* (2013.01); *G06F 3/04883* (2013.01); *G06F 3/04886* (2013.01); *G06F 2203/04104* (2013.01)

(58) Field of Classification Search
    CPC ....... G06F 2203/04104; G06F 3/03547; G06F 3/0412; G06F 3/04845; G06F 3/04883; G06F 3/04886
    See application file for complete search history.

(56) References Cited

U.S. PATENT DOCUMENTS

| | | | |
|---|---|---|---|
| 6,468,212 | B1 | 10/2002 | Scott et al. |
| 6,473,069 | B1 | 10/2002 | Gerpheide |
| 8,593,419 | B2 | 11/2013 | Thorn |
| 8,659,507 | B2 | 2/2014 | Roncalez |
| 10,524,739 | B2 | 1/2020 | Roncalez |
| 2002/0005108 | A1 | 1/2002 | Ludwig |
| 2002/0085668 | A1 | 7/2002 | Blumhofer |
| 2003/0083578 | A1 | 5/2003 | Abe et al. |
| 2003/0105400 | A1 | 6/2003 | Yawata et al. |
| 2004/0150963 | A1 | 8/2004 | Holmberg et al. |
| 2005/0059892 | A1 | 3/2005 | Dubois et al. |
| 2006/0074287 | A1 | 4/2006 | Neumann et al. |
| 2006/0084870 | A1 | 4/2006 | Kim |
| 2006/0173308 | A1 | 8/2006 | Sasaki |
| 2006/0238625 | A1 | 10/2006 | Sasaki |
| 2007/0016029 | A1 | 1/2007 | Donaldson et al. |
| 2007/0230758 | A1 | 10/2007 | Fan |
| 2007/0273671 | A1* | 11/2007 | Zadesky .............. G06F 3/041 345/173 |
| 2007/0294634 | A1 | 12/2007 | Kokemohr |
| 2008/0119731 | A1 | 5/2008 | Becerra et al. |
| 2008/0165141 | A1 | 7/2008 | Christie |
| 2008/0202824 | A1 | 8/2008 | Philipp et al. |
| 2008/0266143 | A1 | 10/2008 | Ohshita et al. |
| 2009/0043195 | A1 | 2/2009 | Poland |
| 2009/0149750 | A1 | 6/2009 | Matsumura |
| 2009/0163814 | A1 | 6/2009 | Amemiya |
| 2009/0177089 | A1 | 7/2009 | Govari et al. |
| 2009/0213141 | A1 | 8/2009 | Gao |
| 2009/0234230 | A1 | 9/2009 | Bercoff et al. |
| 2009/0306514 | A1 | 12/2009 | Imamura |
| 2010/0079404 | A1 | 4/2010 | Degner et al. |
| 2010/0130861 | A1 | 5/2010 | Shimazaki |
| 2010/0139990 | A1 | 6/2010 | Westerman et al. |
| 2010/0179413 | A1 | 7/2010 | Kadour |
| 2011/0043434 | A1 | 2/2011 | Roncalez |
| 2011/0182137 | A1 | 7/2011 | Ozaki |
| 2014/0039317 | A1 | 2/2014 | Sato |
| 2014/0114190 | A1* | 4/2014 | Chiang ................. A61B 8/465 600/440 |
| 2014/0143690 | A1 | 5/2014 | Roncalez |
| 2015/0005630 | A1 | 1/2015 | Jung et al. |
| 2015/0164476 | A1 | 6/2015 | Kong |
| 2015/0209012 | A1 | 7/2015 | Oh et al. |
| 2016/0007965 | A1 | 1/2016 | Murphy |
| 2016/0249884 | A1 | 9/2016 | Hashimoto |
| 2017/0055956 | A1 | 3/2017 | Osumi |
| 2017/0090571 | A1 | 3/2017 | Bjaerum et al. |
| 2017/0220165 | A1 | 8/2017 | Westerman et al. |
| 2018/0172811 | A1 | 6/2018 | Mosegaard |
| 2019/0200965 | A1 | 7/2019 | Couade |

FOREIGN PATENT DOCUMENTS

| | | |
|---|---|---|
| CN | 102405455 | 4/2012 |
| CN | 102713805 A | 10/2012 |
| CN | 103294254 | 9/2013 |
| CN | 103505241 | 1/2014 |
| CN | 104750184 | 7/2015 |
| CN | 105487793 A | 4/2016 |
| CN | 107797654 | 3/2018 |
| DE | 19739284 | 3/1999 |
| EP | 2138103 | 12/2009 |
| EP | 2 921 115 A1 | 9/2015 |
| EP | 3034004 | 6/2016 |
| JP | 09-173333 | 7/1997 |
| JP | 10-248843 | 9/1998 |
| JP | 11-318906 | 11/1999 |
| JP | 2000-316864 | 11/2000 |
| JP | 2002-248099 | 9/2002 |
| JP | 2004033658 | 2/2004 |
| JP | 2005-245961 | 9/2005 |
| JP | 2006513731 | 4/2006 |
| JP | 2006141508 | 6/2006 |
| JP | 2007-087324 | 4/2007 |
| JP | 2007202829 | 8/2007 |
| JP | 2007260188 | 10/2007 |
| JP | 2008-515519 | 5/2008 |
| JP | 2010-142563 | 7/2010 |
| JP | 2010-549131 | 4/2011 |
| JP | 2012061075 | 3/2012 |
| JP | 5208010 | 6/2013 |
| KR | 1020070110352 | 11/2007 |
| KR | 1020100125966 | 12/2010 |
| KR | 10-2011-0079828 | 7/2011 |
| KR | 1020160044401 | 4/2016 |
| KR | 1020190100761 | 8/2019 |
| WO | 99/13396 | 3/1999 |
| WO | 00/31678 | 6/2000 |
| WO | 03/098523 | 11/2003 |
| WO | 2006/035398 | 4/2006 |
| WO | 2006/038182 | 4/2006 |
| WO | 2006/126131 | 11/2006 |
| WO | 2013/148730 A2 | 10/2013 |
| WO | 2015/048327 | 4/2015 |

OTHER PUBLICATIONS

Japanese Office Action for Patent Application No. JP 2014-130249 dated Mar. 31, 2015, 6 pages. .
Japanese Office Action for Patent Application No. 2010-549131 dated Aug. 4, 2015, 20 pages.
Korean Office Action for Patent Application No. 2015-7013069 dated Jun. 15, 2015, 7 pages.
PCT International Search Report in International Application PCT/EP2009/052520, mailed Jun. 16, 2009, 3 pages.
PCT International Search Report in International Application PCT/EP2017/072784, dated Dec. 12, 2017, 5 pages.
Shaaban, Marwa A. et al., "Real-time ultrasound elastography: Does it improve B-mode ultrasound characterization of solid breast lesions?", The Egyptian Journal of Radiology and Nuclear Medicine, Elsevier, Amsterdam, NL, vol. 43, No. 2, Feb. 11, 2012, pp. 301-309.
International Search Report and Written Opinion of the International Searching Authority for International Patent Application No. PCT/IB2018/000580 mailed Nov. 30, 2018, 8 pages.
Hollander et al., "Plane-Wave Compounding in Automated Breast Volume Scanning: A Phantom-Based Study", Ultrasound in Medicine and Biology, 2016, vol. 42, No. 10, pp. 2493-2503.
Korean Notice of Preliminary Rejection in Application 10-2020-7027128, mailed Mar. 17, 2023, 13 pages.
PCT International Preliminary Report on Patentability in International Application PCT/IB2018/000580, mailed Nov. 2, 2020, 7 pages.
European Communication pursuant to Article 94(3) EPC in Application 18740277.1, mailed Apr. 4, 2023, 4 pages.
Chinese 1st Office Action in Application 201880092537.1, mailed Jun. 21, 2023, 13 pages.

* cited by examiner

ULTRASOUND IMAGING SYSTEM

This application is a National Stage Application of PCT/IB2018/000580, filed 24 Apr. 2018, and which application is incorporated herein by reference. To the extent appropriate, a claim of priority is made to the above disclosed application.

FIELD OF THE INVENTION

The present invention concerns an ultrasound imaging system.

BACKGROUND OF THE INVENTION

The present invention concerns more precisely an ultrasound imaging system comprising:
- a probe for emitting and/or receiving ultrasound waves into a medium,
- a processing unit for processing an image on the bases of signals received by said probe,
- a display for visualizing the image processed by the processing unit, and
- a control panel connected to the processing unit for configuring and controlling the processing unit, said control panel comprising input control elements, each one for controlling one system function, and a touch pad for controlling at least a two dimension cursor position on the display.

U.S. Pat. No. 6,135,958 discloses such ultrasound imaging system, that replaces a usual trackball pointing device by a touch pad pointing device. The touch pad is better environmentally sealed, less expensive, generates less stress to the user compared to the trackball solution, and uses less space on the control panel.

However, such touch pad is only used as a pointing device for selecting objects on the display with a tap action.

OBJECTS AND SUMMARY OF THE INVENTION

The object of the present invention is to provide an ultrasound imaging system comprising an improved touch pad so as to have an improved use in terms of comfort and efficiency.

To this effect, the touch pad of the ultrasound imaging system is a multi-touch device that provides multi-touch information to the processing unit, the multi-touch information comprising information of at least two or more touch of user fingers on the touch pad, and the system determines a gesture and an associated system function based on said multi-touch information.

Thanks to these features, the multi-touch information are used to define a plurality of gestures and associated system functions for controlling the ultrasound imaging system. The number of system functions that can be directly used via the touch pad surface is greatly increased.

Then, the user (a doctor, a sonographer) is able to process all necessary actions concerning a complete ultrasound imaging medical examination only via the touch pad. The use is then more comfortable and more efficient (faster).

In various embodiments of the ultrasound imaging system, one and/or other of the following features/aspects may optionally be incorporated.

In one aspect, the system determines at least:
- a tap action when a finger of the user touches the touch pad for a predetermined tap length of time, or
- a click action when a user pushes the touch pad downwardly, and
the system then combines said tap action or click action with the multi-touch information for determining the gesture and associated system function.

A multi-touch information combined with a click action can be then associated to lots of system functions that are the most often used by the user and that are directly executed (e.g. select, run/freeze, save image, save image/video clip).

In one aspect, the associated system function further depends on a contextual configuration that is a memorized system status or a focus on the display.

The number of system functions that can be directly used via the touch pad is again greatly increased.

In one aspect, the touch pad is mounted over a touch pad button so as to provide the click action.

In one aspect, the touch pad button is located at the centre of the touch pad.

In one aspect, the touch pad is mounted over a support member articulated by an hinge into rotation relative to panel casing around a rotation axis parallel to the touch pad, and the support member is mounted over a touch pad button.

In one aspect, the touch pad button and the hinge are distant from each other of a distance greater than 1.5 times the touch pad height.

In one aspect, the touch pad button is located under the touch pad, and preferably near an upper edge of said touch pad.

In one aspect, the support member is articulated by two hinges into rotation around the rotation axis, said hinges being distant from each other of a distance equal to the touch pad width.

In one aspect, the touch pad is mounted over four touch pad buttons, the touch pad buttons being situated near corners of the touch pad.

In one aspect, the touch pad has a touch pad width greater than 10 centimeters.

In one aspect, the touch pad has a touch pad height higher than 5.6 centimeters.

In one aspect, an area of the control panel situated below a lower edge of the touch pad does not comprise any input control element.

In one aspect, the input control elements that are closest to the left edge and the right edge of the touch pad are only input control elements with a low profile.

In one aspect, the system comprises at least two touch pads, a first touch pad and a second touch pad.

In one aspect, the first and second touch pads have the same size.

In one aspect, the first touch pad is for controlling the image on the display and the second touch pad is for controlling the processing unit configuration.

Another object of the present invention is to provide an ultrasound imaging system comprising at least two touch pads, a first touch pad and a second touch pad.

Thanks to these features, the system can increase the number of system functions that can be controlled by the touch pads. These system functions are more rapidly selected and controlled by the user, and the use of the system is more comfortable and more efficient.

In various embodiments of the ultrasound imaging system, one and/or other of the following features/aspects may optionally be incorporated.

In one aspect, the first and second touch pads are multi-touch devices that each one provides multi-touch information to the processing unit, the multi-touch information comprising information of at least two or more touch of user fingers on each touch pad, and the system determines a gesture and an associated system function based on the multi-touch information.

In one aspect, the system determines for each touch pad, at least:
- a tap action when a finger of the user touches the touch pad for a predetermined tap length of time, or
- a click action when a user pushes the touch pad downwardly, and the system then combines said tap action or click action with the multi-touch information for determining the gesture and associated system function.

In one aspect, the first touch pad is for controlling the image on the display and the second touch pad is for controlling the processing unit configuration.

In one aspect, the first and second touch pads have the same size.

Another object of the present invention is to provide an ultrasound imaging system wherein the touch pad is a multi-touch device that provides multi-touch information to the processing unit, and the touch pad has a touch pad width greater than 10 centimeters.

Thanks to these features, the system is able to detect at least four distinct fingers of a user and to generate a huge plurality of various gestures, and each different gesture can be associated to a different system function. The user can control the system most often only with the touch pad, and the use of such system is more comfortable and more efficient.

BRIEF DESCRIPTION OF THE DRAWINGS

Other features and advantages of the invention will be apparent from the following detailed description of two of its embodiments given by way of non-limiting example, with reference to the accompanying drawings. In the drawings:

FIG. 5b is a side view of touch pad of FIG. 5a;

The same numeral references are used to denote identical or similar elements in the various figures. On various figures, axis X, Y, Z are represented for locating the directions.

MORE DETAILED DESCRIPTION

Figure 1:
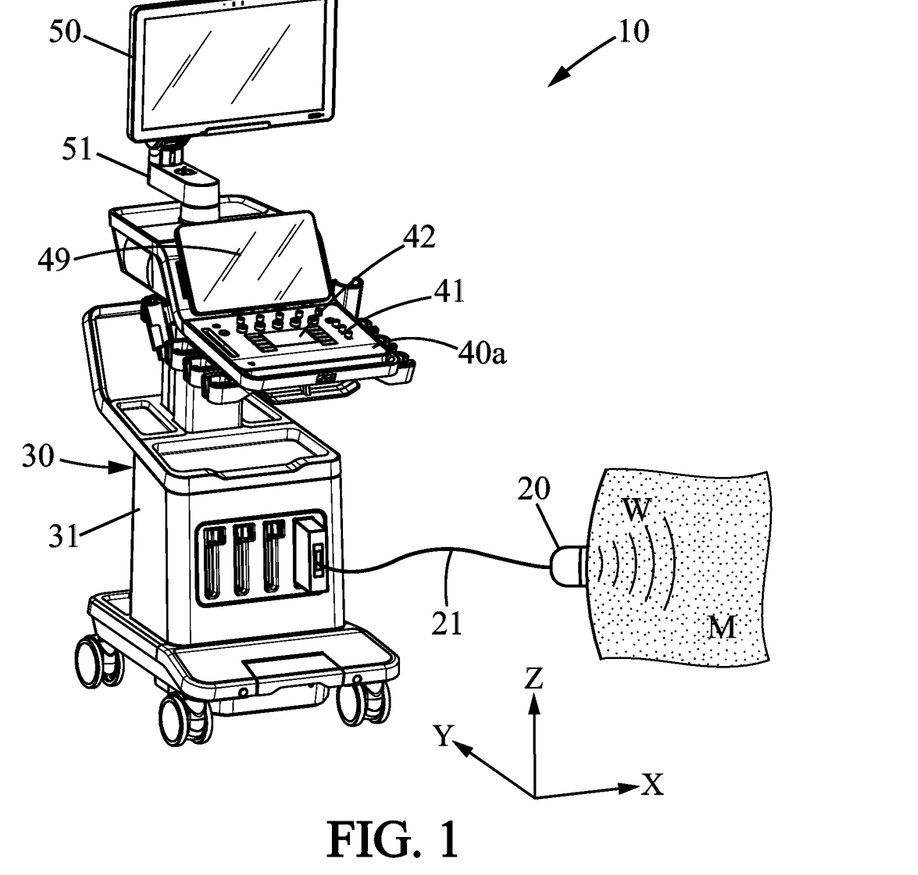
FIG. 1 is a perspective view of an ultrasound imaging system according to the invention.

The FIG. 1 presents an ultrasound imaging system 10 comprising:
- a probe 20,
- a processing unit 30 for processing an image on the bases of signals received by the probe,
- a control panel 40 connected to the processing unit, said control panel at least comprising buttons 41 and a touch pad 42, and
- a display 50 for visualizing the image.

The probe 20 connected to the processing unit 30 via a cable 21 or via a wireless connection, and it is able to emit ultrasound waves W into a medium M and to receive ultrasound waves W from the medium M, said received ultrasound waves being consequent or resulting from reflections of said emitted ultrasound waves on diffusing particles inside said medium. The probe 20 may be a transducer array comprising a plurality of transducers, each one converting an electric signal into a vibration and reciprocally. A transducer is for example a piezoelectric element. The transducer array may comprise hundred transducers or more. The transducer array is a linear or curved and is disposed on an outer surface of the medium M so as to be coupled to the medium and to vibrate and to emit or receive ultrasound waves W.

The processing unit 30 may comprise receiving devices for amplifying and/or filtering signals received from the probe 20, and converters (analog to digital converters and digital to analog converters) for transforming the signals into data representing the signal. The data may be stored into a memory in the processing unit or directly processed for calculating intermediate processed data (beamformed data). The processing unit 30 may use any known processing method to process the image on the bases of the signals received from the probe, such as beamforming. The image processed may be:
- a simple medium image (B-mode image) usually in grey scale for visualizing organs inside the medium, or
- an image showing velocity or flow in the medium (colour image) for example useful for visualizing blood vessels in the medium, or
- an image showing a mechanical characteristic of the medium (elasticity) for example useful for identifying tumours inside the medium.

The display screen 50 is a screen for visualizing the image processed by the processing unit 30. The display 50 may also visualize other information such as scales used in the image, or configuration information for the processing or any information such as help information or contextual gesture help for the touch pad 42.

The display screen may by articulated on a support arm 51 for better positioning for the user. The display screen is usually a screen of a great size (at least 20 inches) for better image visualization to the user.

The control panel 40 is for example a portion of the system casing 31, said portion comprising a panel casing 48 having a substantially flat surface 40a inclined towards the user for manipulation by one hand of said user. The control panel 40 may be moved by a hanger upwards and downward for being adapted to the user size, and may be optionally moved frontward and rearward for being adapted to the user position. As seen on FIG. 1, the control panel 40 may include a control panel display screen 49 for visualizing several configuration information. This control panel display screen 49 can also be hinged to the control panel casing 48 for being inclined into a different inclination than the control panel surface 40a.

Figure 2:
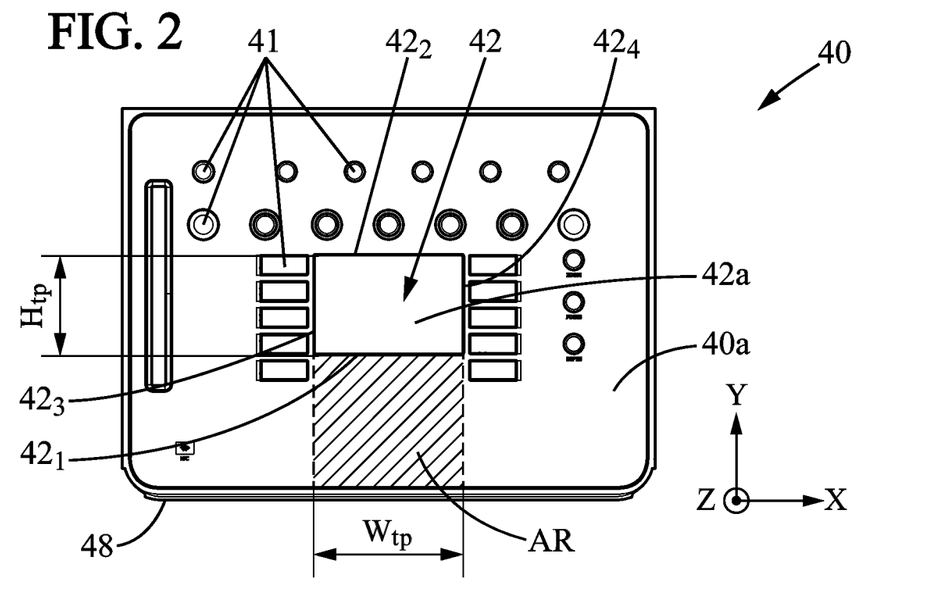
FIG. 2 is an upper view of a first embodiment of a control panel from ultrasound imaging system of FIG. 1.

A first embodiment of a control panel 40 is represented on FIG. 2 and comprises several input control elements that are adapted to input values or adapted to input choices for the processing unit configuration or adapted to control the displayed image or adapted to cause actions.

For example, the input control elements 41 may be chosen in a list comprising:
- a key, touch key, or push button, said key or push button being naturally upwardly urged and having or not a light or sound or tactile feedback when the finger is pressing downwardly said key, said key being adapted to cause an action, a switch button, said switch button having two positions (up and down) for providing a state or choice, a slider cursor, said cursor being movable between two ends for providing a value, a rotary knob, said knob being rotatable for providing a value.

All these input control elements 41 permit to configure and/or to control the processing unit and/or to control the image on the display screen 50. These input control elements 41 provide only one information (one state, one action, one value) for controlling one function of the system/processing unit (one configuration parameter or one action). Examples of such functions are:

a choice of a processing method for the calculation of the image (B-mode, color mode, elastography mode, . . . ), a freeze function to freeze the real time imaging process, a save image or save film (succession of images) function, a measure function, a cursor function, a zoom function, a depth function, a focus function.

These are some of the most usual function for the user to configure and control the processing unit and the image on the display screen.

The control panel 40 further comprises a touch pad 42. Touch pads are well-known devices that detect position of a user finger touch on their flat surface. The touch pad is usually a rectangular shape, but can be a circular shape. This touch pad is preferably positioned near the centre of the control panel surface 40*a*. The touch pad is a pointing device sensing the position of the user finger on its surface and providing at least a two-dimension cursor position in the display screen 50, therefore providing at least two information: x and y coordinates in the touch pad 42 that can be converted into coordinates in the display screen 50.

Additionally, the touch pad 42 can provide the information characterizing that the finger is in contact with the touch pad surface 42*a* or is not in contact with the touch pad surface 42*a*, and the length of time of the contact.

Therefore, the touch pad 42 provides information for deducing actions or action gestures like: a simple tap action, a double tap action or a drag action.

A simple tap action is a gesture in which a user finger touch on the touch pad surface 42*a* is detected for a tap length of time, i.e. a length of time that is short, for example lower than 0.2 seconds. A double tap action is a gesture in which a user finger touch is detected twice, in a sequence comprising a first touch during a tap length of time (as above), a non-detected touch during a undetected length of time, and a second during a tap length of time. The undetected length of time can be equivalent to the tap length of time. A single or double tap will be generally denoted as a tap action, in the following description.

A drag action is gesture in which a user finger is detected on the touch pad surface 42*a*, and the position of this finger is moving on the touch pad surface 42*a* during this uninterrupted touch of said finger. The touch pad 42 records the information of positions of the finger during the drag of the finger on the touch pad surface (until it is lifted and then not detected).

Such touch pad can be used for deducing a simple action at the cursor position, i.e. an action on an element displayed at the determined x-y position on said display screen 50.

Then, on the contrary to the above described input control elements 41 that are devices only providing one information (one state, one action, one value) for controlling one function (one configuration parameter or one action), the touch pad 42 provides a plurality of information. An input control element 41 does not provide any pointing information related a position (x and y) of a user finger on a two dimension surface.

The touch pad 42 has preferably a rectangular shape with a first lower edge $42_1$, a second upper edge $42_2$, a third left edge $42_3$ and a fourth right edge $42_4$. The length of the first and second edges are the touch pad width $W_{tp}$ and the third and fourth edges are the touch pad height $H_{tp}$. Usually, the touch pad width is greater than the touch pad height.

According to the invention, the touch pad 42 is a multi-touch device that provides a multi-touch information to the processing unit 30 for determining multiple finger gestures on the touch pad surface 42*a*, and the system determines a gesture and an associated system function based on said multi-touch information.

Thanks to the above features, the system can detect a great number of gestures

The multi-touch touch pad 42 can detect zero, one or two fingers on the touch surface 42*a*. The multi-touch touch pad 42 is a device that can detect at least two or more fingers on the touch pad surface 42*a*. For example, such touch pad 42 can detect up to four or five fingers on the touch surface. Such multi-touch touch pad 42 detects the positions of detected fingers and the duration of these detections, and then provides these multi-touch information to the system (a connected device).

Eventually, the touch pad 42 detects or determines some predetermined gestures as single or double taps. The multi-touch touch pad 42 provides in real time many information so as the receiving device can use the pre-detected gestures or recognize its own defined gestures.

Preferably, the system determines:

a tap action when a finger of the user touches the touch pad 42 for a predetermined tap length of time, or a click action when a user pushes the touch pad 42 downwardly, and the system then combines said tap action or click action with the multi-touch information for determining the gesture and associated system function.

Thanks to the above features, the system can detect a great number of gestures of the user fingers above the touch pad surface 42*a*. The gesture is a combination of the number of detected fingers, and the movement of these fingers on the touch pad surface 42 (the tap or double tap action, or the fingers slide movement) and the physical click action on the touch pad 42 that moves it downwardly. In case of a slide movement, the system also determines the direction of said slide movement. Therefore, the number of possible combinations, i.e. the number of different gestures that can be determined by the system is quite high, and for example greater than 20.

Each gesture can be associated to a system function of the ultrasound imaging system. Thanks to the above great number, the most of the system functions can be directly done by these gestures on the touch pad 42, without the need for the user to move his hand away from the touch pad 42 for manipulating an input control elements 41. Therefore, the use of the ultrasound imaging system 10 is more efficient and the user can be more easily focused on the probe 20 manipulation above the medium M (a patient) rather than being focused on the control panel 40 manipulation.

The associated system function can be any function that is associated to a physical button of physical input control elements 41 as for example above listed, or any other function not associated to a physical input control element 41.

The physical click action combined to multi-touch information provides a plurality of multi-touch click actions that are very interesting actions for associating them to most important, most used system functions. The physical click gives to the user a feedback that confirms the system function execution. The user can use the system without looking at the touch pad, and then system is then more comfortable and more efficient (faster) for use.

Then, the multi-touch touch pad can be used for complex gesture functions, such as three dimensional (3D) object manipulations, e.g. in case of 3D ultrasound imaging. It can also facilitate four dimensional (4D) manipulations which is 3D with one additional dimension of time.

In fact, multi-touch touch pad 42 gives ability to a huge number of various gestures via all possible sliding parallel or non-parallel displacements of fingers on the touch pad surface 42a.

In fact, for having a huge number of distinct gestures and for having a huge number of associated system functions, the touch pad 42 is preferably able to detect four or five simultaneous fingers on the touch pad surface 42a. Moreover, it is preferable that it detects the slide movement of these fingers on the surface in the four coordinate directions: positive x, negative x, positive y and negative y.

The touch pad may have a width, the touch pad width $W_{tp}$, greater than 10 centimeters so as the system is able to detect at least four fingers of a user. The number of gestures is therefore high. Advantageously the touch pad width $W_{tp}$, greater than 12 centimeters for more comfort to the user.

If necessary, the touch pad 42 width $W_{tp}$ may be greater than 12 centimeters, or even greater than 14 centimeters, therefore increasing the comfort in the use of multiple gestures on this touch pad.

The touch pad 42 may have a height, the touch pad height $H_{tp}$, greater than 5.6 centimeters.

The touch pad aspect ratio $AR_{tp}$ is the ratio of the touch pad width $W_{tp}$ over the touch pad height $H_{tp}$, i.e. $ARtp=W_{tp}/H_{tp}$. The display screen aspect ratio $AR_{ds}$ is the width over the height of said display screen. If the touch pad aspect ratio $AR_{tp}$ is similar to the display screen aspect ratio $AR_{ds}$ at plus or minus ten percent, then a finger position over the touch pad 42 more easily corresponds to a cursor position on the display screen 50.

Figure 3:
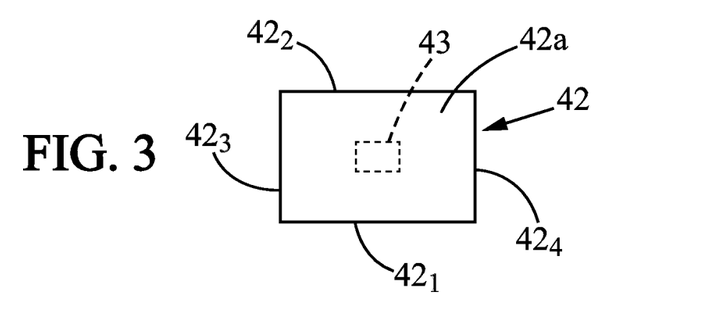
FIG. 3 is an upper view of a first variant of touch pad included in control panel of FIG. 2.

According to a variant as represented on FIG. 3, the touch pad 42 is mounted or fixed above a touch pad button 43, said touch pad button 43 being naturally upwardly urged. Such arrangement provides to the touch pad 42 the click action ability: when a user pushes the touch pad 42 downwardly, the click action is generated by the touch pad button 43 and the system can combine it with the multi-touch information for determining a gesture and an associated system function.

The touch pad button 43 preferably generates a sound and/or a tactile feedback to the user when it is downwardly activated. The touch pad button is not visible to the user as it is under the touch pad. The user can then use the touch pad 42 as a specific touch button (key).

The activation of the touch pad button 43 is a click action that can be used by the processing unit for example as a validation action. Said click action can differs from a simple tap or double tap gesture on the touch pad 42. Thanks to this click action, the touch pad 42 can be more easily used and can be more efficiently used in terms of time spent for controlling or configuring the system.

The gesture is then a combination of the number of detected fingers, the movement of these fingers on the touch pad surface (tap, double tap, slide), and the click action. The number of possible gestures is increased, and most of system functions can be directly associated to them, and the system is more easily used.

More specifically, the gestures can include a combination of number of detected fingers and a click action: It can detect a click action with one finger and a click action with two fingers. It can also detect a click action with any number of fingers from one to five fingers. Each one of these gestures can be associated to a different system function.

Therefore, the click action from the touch pad button 43 is advantageously combined with the multi-touch information from the touch pad 42 for providing gestures that allow more direct control of the system 10. This physical multi-touch click functionality for an ultrasound imaging system helps the user to be more focused on the probe 20 manipulation over the medium (patient). Such functionality improves user comfort.

More specifically, the gestures can include a combination of number of detected fingers and a movement of these fingers. It can detect a simultaneous movement of one, two or any number of fingers on the touch pad surface 42a. Each one of these gestures can also be associated to a different system function. The fingers movements can be parallel to each other or not parallel to each other. For example, a convergent movement of two fingers can be associated to a zoom out system function, while a divergent movement of two fingers can be associated to a zoom in system function.

Additionally, each gesture can be associated to a plurality of system functions. The processing unit 30 then determines the system function to be associated and executed on the bases of the determined gesture and also on the bases of a contextual configuration: a status of the system or a focused object on the control panel display screen 49 or the display screen 50. A system status may be a functioning mode of the system 10 that is determined by previous actions by the user on the input control elements 41 and/or touch pad 42.

Figure 7:
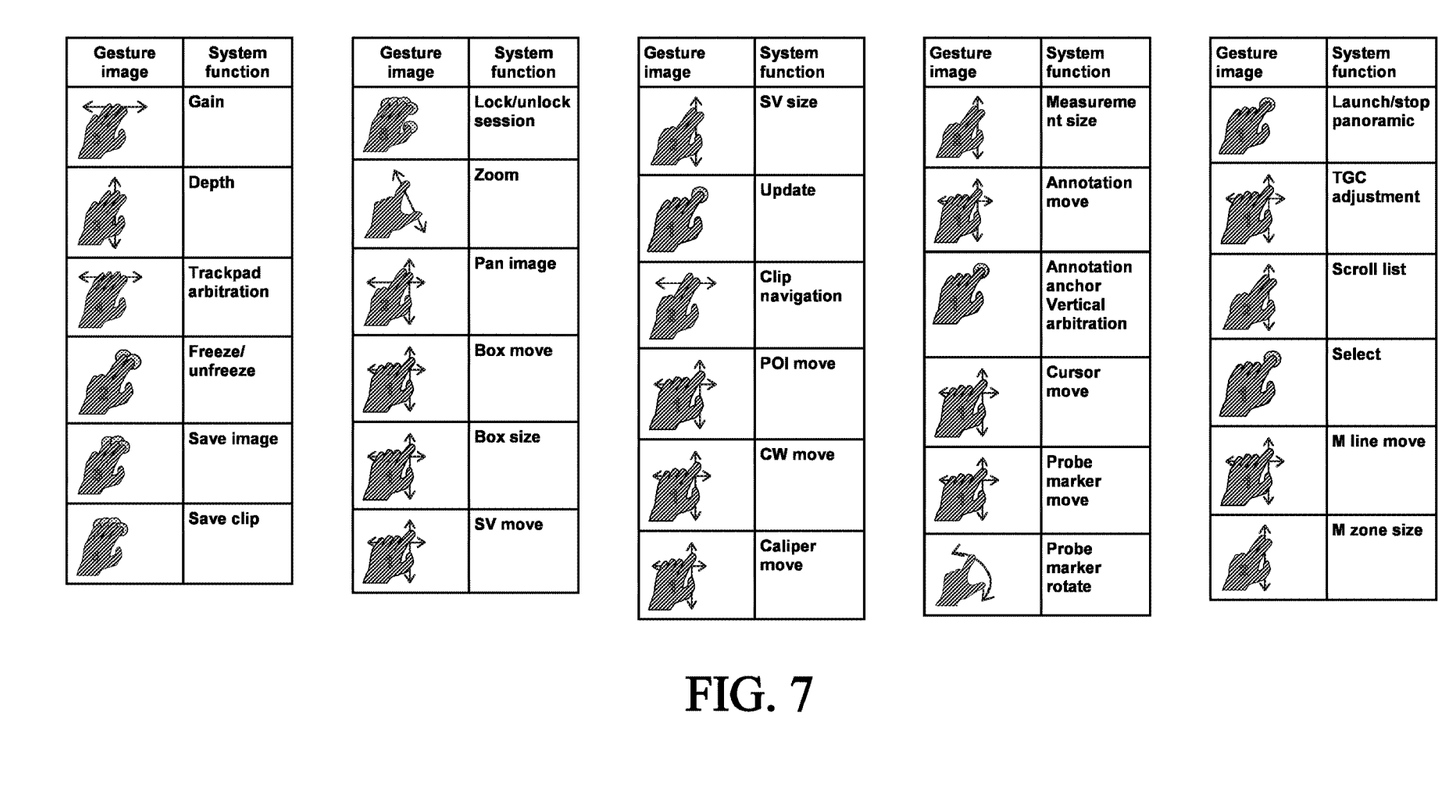
FIG. 7 is an example of a table associating a gesture to a system function.

The FIG. 7 shows an example of tables associating a gesture to a system function. In these tables, there are 30 gestures. The gesture image shows a hand:
- with circles at the end of fingers that are touching the touch pad surface 42a and activating for a click action (for e.g. via the touch pad button 43 activation), or
- with arrows for a slide action.

The number inside the hand remembers the number of fingers touching the touch pad surface 42a.

Some gestures are represented twice: for two system functions. In that case, the system chooses one of them on the bases of a memorized contextual configuration as explained above.

The touch pad button 43 can be positioned in the center of the touch pad surface 42a so that the user feels the touch pad 42 as only a single touch button.

The control panel 40 comprises below the first lower edge $42_1$ of the touch pad 42 an area AR that does not comprise any input control element 41. The user can then put down on this area AR the palm of his hand when manipulating the touch pad 42: This will not interfere with any input control element 41.

Additionally, the input control elements 41 that are closest to the third left edge $42_3$ and the fourth right edge $42_4$ are only input control elements 41 with a low profile (low height above the control panel surface 40a). For example, these closest input control elements 41 are only push or switch buttons. The user hand is then less limited in its lateral movements. Optionally, the input control elements 41 that are closest to the second upper edge 42$_2$ and third left edge 42$_3$ and the fourth right edge 42$_4$ are only input control elements 41 with a low profile to free the depth (Y) and lateral (X) hand movements above the touch pad 42.

Then, the input control elements 41 that more distant than said close input control elements comprises at least one rotary knob.

Figure 4:
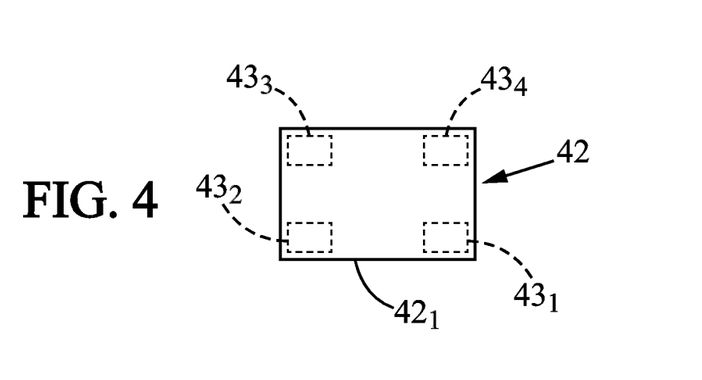
FIG. 4 is an upper view of a second variant of touch pad included in control panel of FIG. 2.

According to a variant as represented on FIG. 4, the touch pad 42 is mounted or fixed above a plurality of touch pad buttons, said touch pad buttons being naturally upwardly urged. Such arrangement provides to the touch pad 42 the click action ability: when a user pushes the touch pad 42 downwardly, the click action is generated by at least one of the touch pad buttons 43 and the system can combine it with the multi-touch information for determining a gesture and an associated system function.

As in the previous variant, at least one of the touch pad buttons preferably generates a sound and/or a tactile feedback to the user when it is downwardly activated. The touch pad buttons are not visible to the user as they are under the touch pad 42. The user can then use the touch pad 42 as a specific touch button (key).

The activation of the touch pad button 43 is a click action that can be used by the processing unit as a validation action in a gesture, as explained in the first variant.

The gesture is a combination of the number of detected fingers, the movement of these fingers on the touch pad surface (tap, double tap, slide), and the click action. As explained above, this combination provides a great number of gestures that can be directly associated to system functions.

Advantageously, there are four touch pad buttons 43$_1$, 43$_2$, 43$_3$, 43$_4$, positioned at the corners of the touch pad 42, so as to improve stability of the touch pad activation when pressing it down.

Figure 5A:
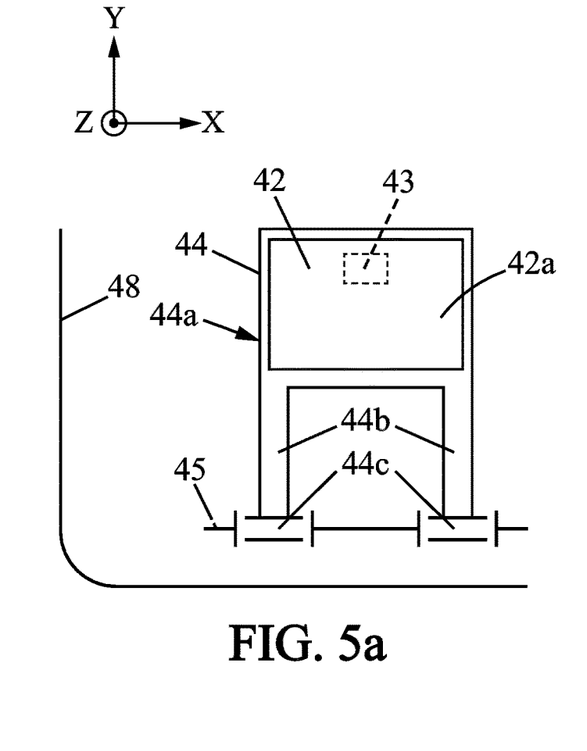
FIG. 5a is an upper view of a third variant of touch pad included in control panel of FIG. 2.
Figure 5B:
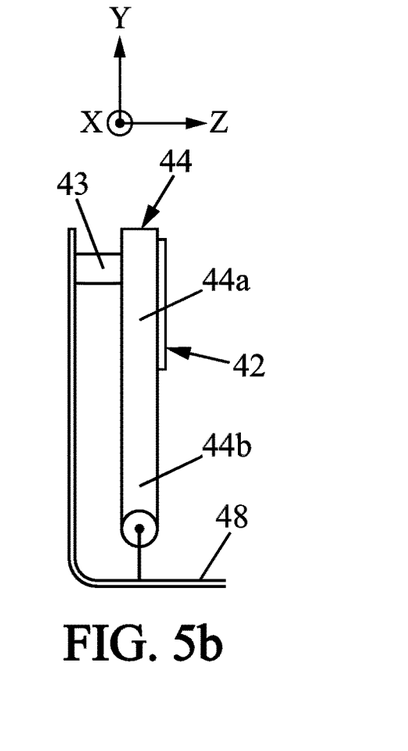

According to a variant as represented on FIGS. 5*a* and 5*b*, the touch pad 42 is mounted or fixed above a support member 44. The support member comprises a first portion 44*a* having a flat shape adapted to receive the touch pad 42: The first portion 44*a* has substantially the same shape and same size of said touch pad 42. This first portion 44*a* extends downward into one or two arms 44*b* down to respectively one or two hinges 44*c*. The hinge 44*c* has a rotation axis 45 relative to the panel casing 48 for allowing rotation of the support member and touch pad assembly relative to said panel casing 48. The support member 44 is further mounted or fixed above a touch pad button 43. The touch pad button 43 is for example situated near the second upper edge 42$_2$ of said touch pad 42.

Such arrangement provides to the touch pad 42 the click action ability: when a user pushes the touch pad 42 downwardly, the click action is generated by the touch pad button 43 and the system can combine it with the multi-touch information for determining a gesture and an associated system function.

Then, the touch pad 42 is naturally upwardly urged. The touch pad button 43 preferably generates a sound and/or a tactile feedback to the user when it is downwardly activated. The touch pad button is not visible to the user as it is under the touch pad. The user can then use the touch pad 42 as a specific touch button (key).

The activation of the touch pad button 43 is a click action that can be used by the processing unit as a validation action, as explained in the first and second variants.

The activation of the touch pad button 43 is a click action that can be used by the processing unit for example as a validation action in a gesture, as explained in the first variant.

The gesture is a combination of the number of detected fingers, the movement of these fingers on the touch pad surface (tap, double tap, slide), and the click action. As explained above, this combination provides a great number of gestures that can be directly associated to system functions.

Thanks to this variant, the touch pad 42 is suspended in a rotating mechanism that is as simple as in the first variant and having more stability as in the second variant.

In case of one hinge, the hinge 44*c* preferably has a length substantially equal to the touch pad width $W_{tp}$ so as to have good mechanism stability.

In case of two hinges (left and right), these hinges have same common rotation axis 45. The hinges can be distant from each other of a distance substantially equal to the touch pad width $W_{tp}$ as represented on the figure. This structure improves the mechanism stability.

The distance between the touch pad button 43 and the rotation axis 45 is higher than the touch pad height $H_{tp}$, and preferably greater than 1.5 times the touch pad height $H_{tp}$. The angle of rotation of said assembly is small and the user substantially feels only a translation in a direction perpendicular to the touch pad surface 42*a*.

The arms 44*b* and hinges 44*c* of the support member 44 are located inside the panel casing at the area AR under the first lower edge 42$_1$ of the touch pad 42. As this area AR does not comprises any input control element 41 this mechanism can be integrated inside the panel casing 48.

Then according to all the above variants, the touch pad 42 is mounted over a touch pad button 43. This means that the touch pad is suspended directly or indirectly above one or a plurality of touch pad buttons.

Thanks to this particular feature, the activation of the touch pad button 43 is a click action that can be used by the processing unit as a validation action. The tap and the double tap gestures done on the touch pad 42 differ from the click action on the touch pad button 43. In fact, the click action is a sort of tap gesture produced with an higher force on the touch pad 42 (and eventually a longer time duration) so that the touch pad button 43 on which the touch pad 42 is suspended, is actuated for generating the click action. The consequence of the click action is a small vertical (Z) displacement of whole touch pad 42 in direction of touch pad button 43 (perpendicular to the touch pad surface), and a sound and/or a tactile feedback to the user to feel said click action (without any doubt).

Figure 6:
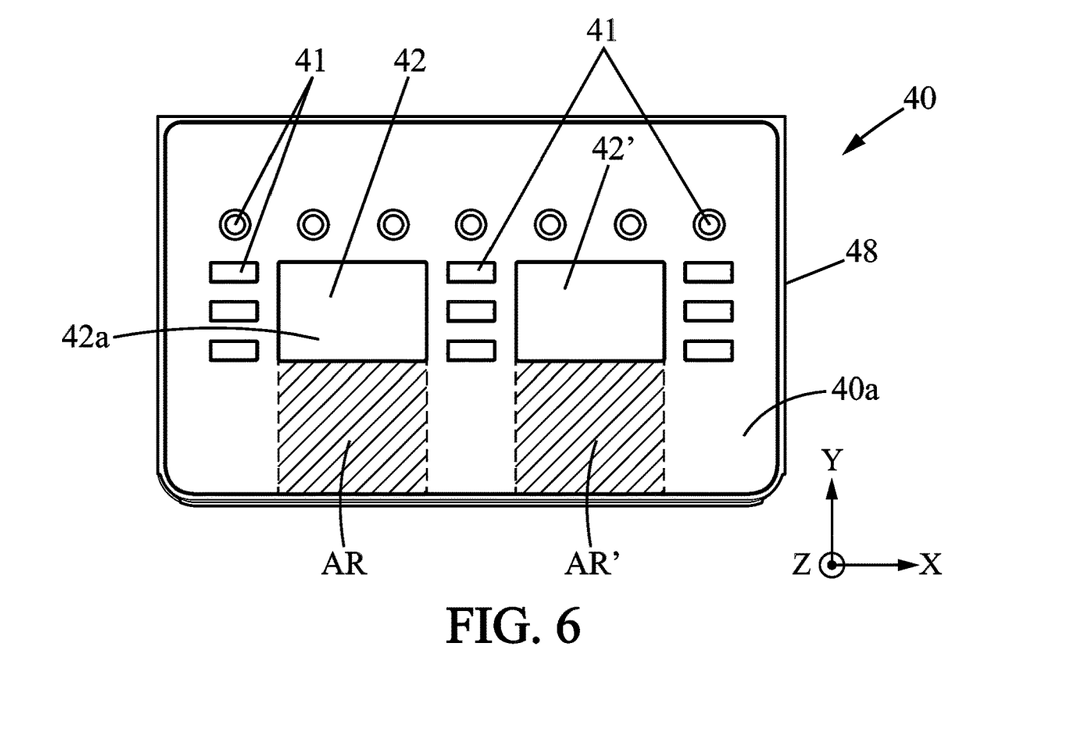
FIG. 6 is an upper view of a second embodiment of a control panel from ultrasound imaging system of FIG. 1.

A second embodiment of a control panel is represented on FIG. 6: this control panel 40 comprises two touch pads, a first touch pad 42 and a second touch pad 42'.

Such feature can also be used independently from the others, and more precisely independently from the click action feature. Thanks to this features, the system can increase the number of system functions that can be controlled by the touch pads. These system functions are more rapidly selected and controlled by the user, and the use of the system is more comfortable and more efficient. The two touch pads helps to reduce the number of physical buttons on the control panel, and to provide a simpler and cheaper system without reducing the comfort of use.

However, the first and second touch pads 42, 42' may also be multi-touch devices that each one provides multi-touch information to the processing unit. Each touch pad 42, 42' also generates a click action when a user pushes each touch pad downwardly, and each click action can be combined with the corresponding multi-touch information (from the concerned touch pad) for determining a gesture and an associated system function. Such arrangement is then of comfortable and more efficient for the user.

The control panel 40 comprises below the first lower edge of the first touch pad 42 an area AR, and below the first lower edge of the second touch pad 42' an area AR'. Preferably, the areas AR and AR' do not comprise any input control element 41 on them. The user can then put down on these areas AR, AR' the palm of his hand when manipulating the touch pads 42, 42': This will not interfere with any input control element 41.

In case of the variant of FIGS. 5*a*, 5*b*, the mechanisms including the arms and hinges of support members of each touch pad 42, 42' can be located and integrated inside the panel casing 48 at the areas AR, AR'.

The first and second touch pads 42, 42' may have the same size.

The first touch pad 42 is for example adapted for controlling the image on the display 50 and the second touch pad 42' is for controlling the processing unit configuration.

The invention claimed is:

1. An ultrasound imaging system comprising:
a probe for emitting and/or receiving ultrasound waves into a medium,
a processing unit for processing an image on the basis of signals received by said probe,
a display for visualizing the image processed by the processing unit, and
a control panel connected to the processing unit for configuring and controlling the processing unit, said control panel comprising a plurality of buttons, each button being configured to control one system function, and a touch pad for controlling at least a two dimensional cursor position on the display, and wherein:
the touch pad is a multi-touch device that provides multi-touch information to the processing unit, the multi-touch information comprising information of at least two or more touch of user fingers on the touch pad, and
the system determines a gesture and an associated system function based on said multi-touch information, and the system determines at least one of:
a tap action when a finger of the user touches the touch pad for a predetermined tap length of time, or
a click action when the user pushes the touch pad downwardly, the click action providing a physical feedback to the user, and
the system then combines the at least one of the tap action or the click action with the multi-touch information for determining the gesture and the associated system function, and
the touch pad is mounted over a touch pad button so as to provide the click action, the touch pad button being distinct from the touch pad, wherein the touch pad is configured such that upon receiving a downward pressure on a portion thereof that is over the touch pad button with sufficient force, the touch pad undergoes a displacement towards the touch pad button, and the touch pad button is activated to provide the click action;
wherein:
the touch pad is mounted over a support member articulated by a hinge into rotation relative to a panel casing around a rotation axis parallel to the touch pad, and the support member is mounted over the touch pad button; and
the touch pad button and the hinge are distant from each other by a distance greater than a touch pad length along a direction connecting the touch pad button to the hinge.

2. The system according to claim 1, wherein said click action is a physical click action corresponding to a displacement of the whole touch pad in direction of the touch pad button.

3. The system according to claim 1, wherein the associated system function further depends on a contextual configuration that is a memorized system status or a focus on the display.

4. The system according to claim 1, wherein the touch pad button is located at a centre of the touch pad.

5. The system according to claim 1, wherein the touch pad button and the hinge are distant from each other of a distance greater than 1.5 times the touch pad length along the direction connecting the touch pad button to the hinge.

6. The system according to claim 1, wherein the support member is articulated by two hinges into rotation around the rotation axis, the two hinges being distant from each other of a distance equal to the touch pad width.

7. The system according to claim 1, wherein the touch pad is mounted over four touch pad buttons, the four touch pad buttons being situated near corners of the touch pad.

8. The system according to claim 1, wherein the touch pad has a touch pad width greater than 10 centimeters.

9. The system according to claim 8, wherein the touch pad length higher than 5.6 centimeters.

10. The system according to claim 1, wherein the plurality of buttons that are closest to a left edge and a right edge of the touch pad are only buttons with a low profile.

11. The system according to claim 1, comprising at least a first touch pad and a second touch pad.

12. The system according to claim 11, wherein the first and second touch pads have the same size.

13. The system according to claim 11, wherein the first touch pad is for controlling the image on the display and the second touch pad is for controlling a configuration of the processing unit.

14. The system according to claim 11, wherein the first and second touch pads are multi-touch devices, wherein each one of the first and second touch pads provides multi-touch information to the processing unit, the multi-touch information of the first and second touch pads comprising information of at least two or more touch of user fingers on each touch pad, and the system determines the gesture and the associated system function based on said multi-touch information of the first and second touch pads.

15. The system according to claim 1, wherein the touch pad button is located near an upper edge of the touch pad.

16. The system according to claim 1, wherein the touch pad button is configured to be urged towards the touch pad.

17. The system according to claim 1, wherein the touch pad button is separated from the touch pad by the support member.

18. An ultrasound imaging system comprising:
a probe for emitting and/or receiving ultrasound waves into a medium,
a processing unit for processing an image on the basis of signals received by said probe,
a display for visualizing the image processed by the processing unit, and a control panel connected to the processing unit for configuring and controlling the processing unit, said control panel comprising a plurality of buttons, each button being configured to control one system function, and a touch pad for controlling at least a two dimensional cursor position on the display, and wherein:

the touch pad is a multi-touch device that provides multi-touch information to the processing unit, the multi-touch information comprising information of at least two or more touch of user fingers on the touch pad, and the system determines a gesture and an associated system function based on said multi-touch information, and the touch pad is mounted over a touch pad button so as to provide a click action, the touch pad button being distinct from the touch pad, wherein the touch pad is configured such that upon receiving a downward pressure on a portion thereof that is over the touch pad button with sufficient force, the touch pad undergoes a displacement towards the touch pad button, and the touch pad button is activated to provide the click action;

wherein:

the touch pad is mounted over a support member articulated by a hinge into rotation relative to a panel casing around a rotation axis parallel to the touch pad, and the support member is mounted over the touch pad button; and the touch pad button and the hinge are distant from each other by a distance greater than a touch pad length along a direction connecting the touch pad button to the hinge.

19. The system according to claim 18, wherein the touch pad button and the hinge are distant from each other of a distance greater than 1.5 times the touch pad length along the direction connecting the touch pad button to the hinge.

* * * * *